(12) United States Patent
Chodkowski et al.

(10) Patent No.: US 11,583,649 B2
(45) Date of Patent: Feb. 21, 2023

(54) PATIENT INTERFACE DEVICE COMPONENT DESIGN SELECTION OR GENERATION SYSTEMS AND METHODS

(71) Applicant: KONINKLIJKE PHILIPS N.V., Eindhoven (NL)

(72) Inventors: Lauren Patricia Chodkowski, Pittsburgh, PA (US); Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 734 days.

(21) Appl. No.: 16/585,107

(22) Filed: Sep. 27, 2019

(65) Prior Publication Data

US 2020/0101249 A1 Apr. 2, 2020

Related U.S. Application Data

(60) Provisional application No. 62/737,385, filed on Sep. 27, 2018.

(51) Int. Cl.
| | |
|---|---|
| *G06K 9/00* | (2022.01) |
| *A61M 16/06* | (2006.01) |
| *G16H 10/20* | (2018.01) |
| *A61B 5/00* | (2006.01) |
| *G06T 19/20* | (2011.01) |

(52) U.S. Cl.
CPC ....... *A61M 16/0611* (2014.02); *A61B 5/0064* (2013.01); *G06T 19/20* (2013.01); *G16H 10/20* (2018.01); *A61M 2016/0661* (2013.01); *A61M 2207/00* (2013.01); *G06T 2219/2021* (2013.01)

(58) Field of Classification Search
CPC .... G06V 40/165; G06V 10/454; G06V 10/82; G06V 20/17; G06V 20/58; G06V 40/171; A62B 18/02; A62B 27/00; A62B 18/084; A62B 18/08; A62B 17/006; A62B 18/025; A62B 23/02
See application file for complete search history.

(56) References Cited

U.S. PATENT DOCUMENTS

| | | | | |
|---|---|---|---|---|
| 2005/0268907 | A1* | 12/2005 | McFarlane | A62B 18/00 128/201.24 |
| 2014/0278319 | A1* | 9/2014 | Thiruvengada | G06F 30/20 703/11 |
| 2019/0232013 | A1 | 8/2019 | Yu et al. | |

* cited by examiner

*Primary Examiner* — Alex Kok S Liew
(74) *Attorney, Agent, or Firm* — Michael W. Haas

(57) ABSTRACT

A method of selecting or generating a design for a component of a patient interface device, the method including receiving a scan of at least a portion of a patient's face, receiving preference information about the patient, and generating a custom design or selecting a preexisting design for the component of the patient interface device based on the scan of at least a portion of the patient's face and the preference information, wherein a size or shape of the generated custom design for the component or selected preexisting design for the component is based on the preference information.

12 Claims, 3 Drawing Sheets

PATIENT INTERFACE DEVICE COMPONENT DESIGN SELECTION OR GENERATION SYSTEMS AND METHODS

CROSS-REFERENCE TO RELATED APPLICATIONS

This patent application claims the priority benefit under 35 U.S.C. § 119(e) of U.S. Provisional Application No. 62/737,385, filed on Sep. 27, 2018, the contents of which are herein incorporated by reference.

BACKGROUND OF THE INVENTION

1. Field of the Invention

The present invention pertains to a patient interface device selection or creation systems and methods, and, in particular, to systems or methods for using scan data with additional criteria for selecting or creating a component of a patient interface device.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow followed by oxyhemoglobin desaturation and/or a cortical arousal. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a positive airway pressure (PAP) to the patient's airway using an airway pressure support system that typically includes a mask, a pressure generating device, and a conduit to deliver positive pressure breathing gas from the pressure generating device to the patient through the mask. This positive pressure effectively "splints" the airway, thereby maintaining an open passage to the lungs. In one type of PAP therapy, known as continuous positive airway pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

It is important that the patient interface device fits the patient. An improper fit can lead to a patient interface device that does not properly seal against the patient's face, which can cause to leaks that are detrimental to the patient's pressure support therapy. Additionally, a properly fitting patient interface device should be comfortable for the patient to wear. A patient interface device that does not fit properly could cause discomfort due to being too tight, rubbing against certain points on the patient's face, or other uncomfortable symptoms of an improper fit. The discomfort can lead to the patient choosing to discontinue pressure support therapy.

SUMMARY OF THE INVENTION

In accordance with an aspect of the disclosed concept, a method of selecting or generating a design for a component of a patient interface device comprises: receiving a scan of at least a portion of a patient's face; receiving preference information about the patient; generating a custom design or selecting a preexisting design for the component of the patient interface device based on the scan of at least a portion of the patient's face and the preference information, wherein a size or shape of the generated custom design for the component or selected preexisting design for the component is based on the preference information.

In accordance with another aspect of the disclosed concept, a system comprises: a face scanning unit structured to obtain a scan of at least a portion of a patient's face; a patient preference collection unit structured to obtain preference information about the patient; a patient interface selection unit structured to generate a custom design or select a preexisting design for a component of a patient interface device for the patient based on the scan of at least a portion of the patient's face and the preference information, wherein a size or shape of the generated custom design for the component or the selected preexisting design for the component is based on the preference information; and an output unit structured to output the custom cushion information or the cushion selection information.

In accordance with another aspect of the disclosed concept, a non-transitory computer readable medium stores one or more programs, including instructions, which when executed by a computer, causes the computer to perform a method of selecting or generating a design for a component of a patient interface device. The method comprises: receiving a scan of at least a portion of a patient's face; receiving preference information about the patient; and generating a custom design or selecting a preexisting design for the component of the patient interface device based on the scan of at least a portion of the patient's face and the preference information, wherein a size or shape of the generated custom design for the component or the selected preexisting design for the component is based on the preference information.

DETAILED DESCRIPTION OF EXEMPLARY EMBODIMENTS

Figure 1:
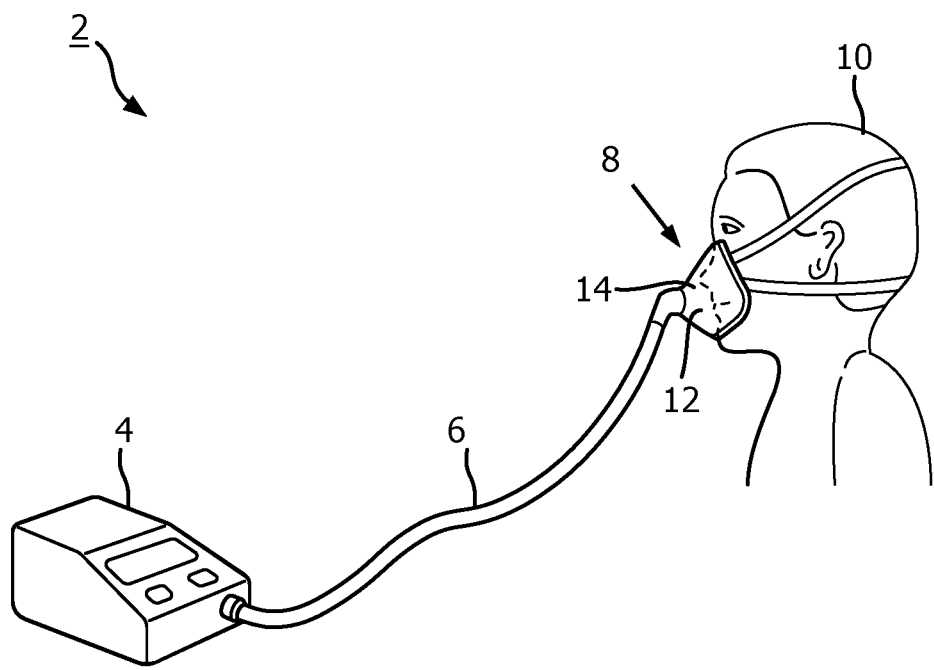
FIG. 1 is a diagram of a pressure support system according to an exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient is generally shown in FIG. 1. System 2 includes a pressure/flow generator 4, a delivery conduit circuit 6, a patient interface device 8 and a headgear 10 for securing patient interface device 8 to the head of a patient (not numbered). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

In the illustrated example system 2 of FIG. 1, patient interface device 8 is depicted as a nasal/oral mask which includes a patient sealing assembly in the form of a cushion 12 coupled to a generally rigid frame member of faceplate 14 which may be coupled to conduit 6 either directly or indirectly via any suitable coupling mechanism.

Figure 2:
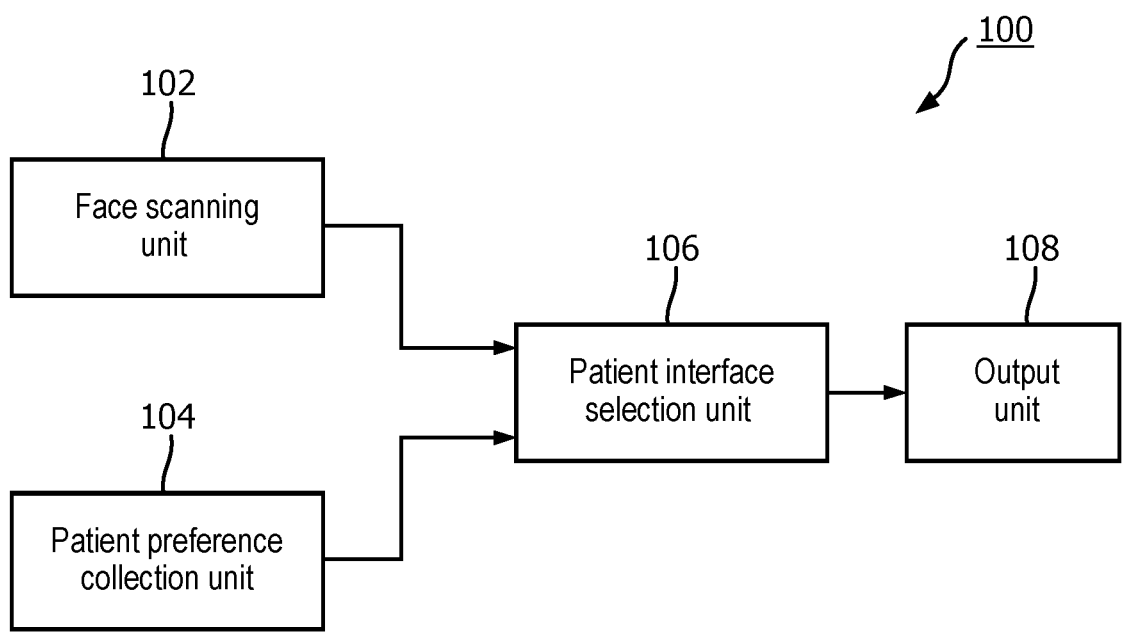
FIG. 2 is a schematic diagram of a patient interface device component design selection or generation system according to an exemplary embodiment of the disclosed concept.

FIG. 2 is a schematic diagram of a system 100 for selecting, creating, or modifying designs for one or more components of a patient interface device in accordance with an example embodiment of the disclosed concept. System 100 may be used, for example and without limitation, to select, create, or modify a cushion design for a patient interface device for use in a system adapted to provide a regimen of respiratory therapy to a patient, such as system 2 shown in FIG. 1. System 100 may also be used select, create, or modify designs for other components for patient interface devices. It will be appreciated by those having ordinary skill in the art that components designs selected, created, or modified using system 100 may be employed in other types of respiratory therapy systems or other types of systems where a patient interface device or cushion is employed.

System 100 includes a face scanning unit 102, a patient preference collection unit 104, a patient interface selection unit 106, and an output unit 108. Face scanning unit 102 is structured to scan a patient's face and to create model, such as a 3-D model, of the patient's face. Face scanning unit 102 may be, without limitation, a 3-D optical scanner, a camera, a push-pin array, or any other device suitable for creating a model of the patient's face. Face scanning unit 102 is structured to output the model of the patient's face to patient interface selection unit 106.

Patient preference collection unit 104 is structured to obtain one or more patient preferences. Patient preferences may be a variety of types of preferences the patient has generally or in relation to respiratory therapy. For example, one type of patient preference is the patient's preference regarding what is most important in patient interface device performance. For example, the patient may provide a personal ranking of patient interface device performance characteristics such as, without limitation, seal, comfort, stability (e.g., side-to-side stability), and appeal. Another example of a patient preference that may be collected is type of fit. For example, the patient may select their preference between loose, standard, and snug fits. Yet another example of a patient preference may be the patient's disposition regarding claustrophobia related to wearing a patient interface device. For example, the patient may rank their level of claustrophobia while wearing a patient interface device from 1 to 10. However, it will be appreciated that other rankings of preferences may be used without departing from the scope of the disclosed concept. In another example, may rank their feeling of restricted breathing when breathing only through their nose. For example, the patient may indicate that they feel no restriction, that they feel a slight restriction, or that they feel a severe restriction.

While some examples of types of patient preferences are provided above, it will be appreciated by those having ordinary skill in the art that any other types of patient preferences relevant to use of a patient interface may be collected by patient preference collection unit 104 without departing from the scope of the disclosed concept. It will also be appreciated that any number of patient preferences may be collected without departing from the scope of the disclosed concept. Patient preference collection unit 104 is structured to provide the collected patient preferences to patient interface selection unit 106.

Patient preference collection unit 104 may be any type of device suitable for collection of patient preference information from a patient. For example and without limitation, patient preference collection unit 104 may be an electronic device, such as a computer, tablet, phone, or any other suitable type of device where a patient or another party may enter the patient preference information. In some example embodiments, patient preference collection unit 104 may provide a user interface to guide the process of collection patient preference information. For example and without limitation, the user interface may provide questions or prompts and allow the user to select answers through the user interface. For example, the user interface may ask the user what type of fit they prefer and allow the user to select between the answers loose, standard, and snug. However, it will be appreciated that any other suitable manner of collecting patient preference information may be employed without departing from the scope of the disclosed concept.

Patient interface selection unit 106 is structured to receive the model of the patient's face from face scanning unit 102 and the patient preference information from patient preference collection unit 104. In an embodiment, patient interface selection unit 106 is structured to generate a custom design for a component of a patient interface device or select a preexisting design for a component of patent interface device based on the model of the patient's face and the preference information. The size or shape of the generated custom design or the selected preexisting design for the component is based on the preference information. For example, in an exemplary embodiment, patient interface selection unit 106 is structured to generate information on a base design for a component of a patient interface device based on the model of the patient's face and the patient preference information. The base design for the component may be an optimally fitting component based on the model of the patient's face. The base design for the component may be generated based on an analysis of the model of the patient's face to be an optimally fitting component. Any suitable analysis method may be used to determine the base design. In some exemplary embodiments, the base design for the component is custom generated. In some other exemplary embodiments, the base design for the component is selected from a preexisting set of designs. For example, patient interface selection unit 106 selects a design from a database that optimally fits the patient based on an analysis of the model of the patient's face.

Once the base design for the component has been selected, patient interface selection unit 106 adjusts the size or shape of the base design based on the preference information of the patient collected from patient preference collection unit 104. For example, in an embodiment, the preference information includes mask performance importance such as whether seal, comfort, or side-to-side stability is most important. When comfort is ranked above a predetermined threshold of importance, the size of the base design is increased in length and width by predetermined amounts (e.g., without limitation, 2%). In an embodiment, the preference information includes a type of fit preference, such as loose, standard, or snug. When the type of fit preference is loose, the size of the base design is increased in length and width by predetermined amounts (e.g., without limitation, 2%). When the type of fit preference is snug, the size of the base design is decreased in length and width by a predetermined amount (e.g., without limitation, 2%). In some examples, when the type of fit is standard, the size of the base design is not changed. In an embodiment, the preference information includes a claustrophobia rating (e.g., 1-10, or any other suitable rating system). When the claustrophobia rating is above a predetermined threshold level, the size of the base design is adjusted such that a visual size of the base design is decreased by a predetermined amount.

In an embodiment, the preference information includes a nose breathing restriction rating (e.g. no restriction, slight restriction, severe restriction). When the nose breathing restriction rating is above a first threshold level (e.g., a slight restriction), the size of an opening of the base design is increased in length and width by first predetermined amounts (e.g., 5%). When the nose breathing restriction rating is above a second threshold level (e.g., a severe restriction), the size of an opening of the base design is increased in length and width by second predetermined amounts (e.g., 7%). A contact angle of the base design may also be decreased by a predetermined amount (e.g., 2%) to decrease contact on sides of the alare of a patient.

The size or shape of the base design may be adjusted in any suitable manner based on the preference information. In an embodiment, the base design is a custom design generated by patient interface selection unit 106 based on the model of the patient's face. The base design is then morphed to adjust its size based on the preference information. In another embodiment, the base design is selected from preexisting designs based on the 3-D model of the patient's face. In this example, the preexisting designs each have several size or shape options. The base design is adjusted in size or shape based on the preference information. Then, a new size option of the preexisting design is selected based on the size adjusted base cushion design. For example, one size preexisting design is selected based on the scan of the patient face, and then a larger size option is instead selected based on the preference information indicating that a loose fit is preferred. Patient interface selection unit 106 may generate a custom design for the component based on the size adjusted base design or identification information for the selected preexisting design according to embodiments of the disclosed concept.

In some embodiments, patient interface selection unit 106 may be implemented by a processor executing a routine. The processor may have an associated memory where the routine is stored. Executing the routine may cause the processor to implement the functionality of patient interface selection unit 106, such as generating a base design for the component and adjusting a size or shape of the base design based on the preference information. Patient interface selection unit 106 may be embodied in any suitable type of electronic device such as, without limitation, a computer, tablet, phone, or any other suitable type of device.

Output unit 108 is structured to output the custom design information or the identification information generated by patient interface selection unit 106. Output unit 108 may be any suitable device for outputting information. In some exemplary embodiments, output unit 108 may be a display. However, it will be appreciated that other types of devices suitable for outputting information may be employed without departing from the scope of the disclosed concept.

It will be appreciated that the component of the patient interface device may be any component of a patient interface device. In some embodiment, the component is a cushion. It will also be appreciated that the disclosed concept may be applied to multiple components of a patient interface device.

Figure 3:
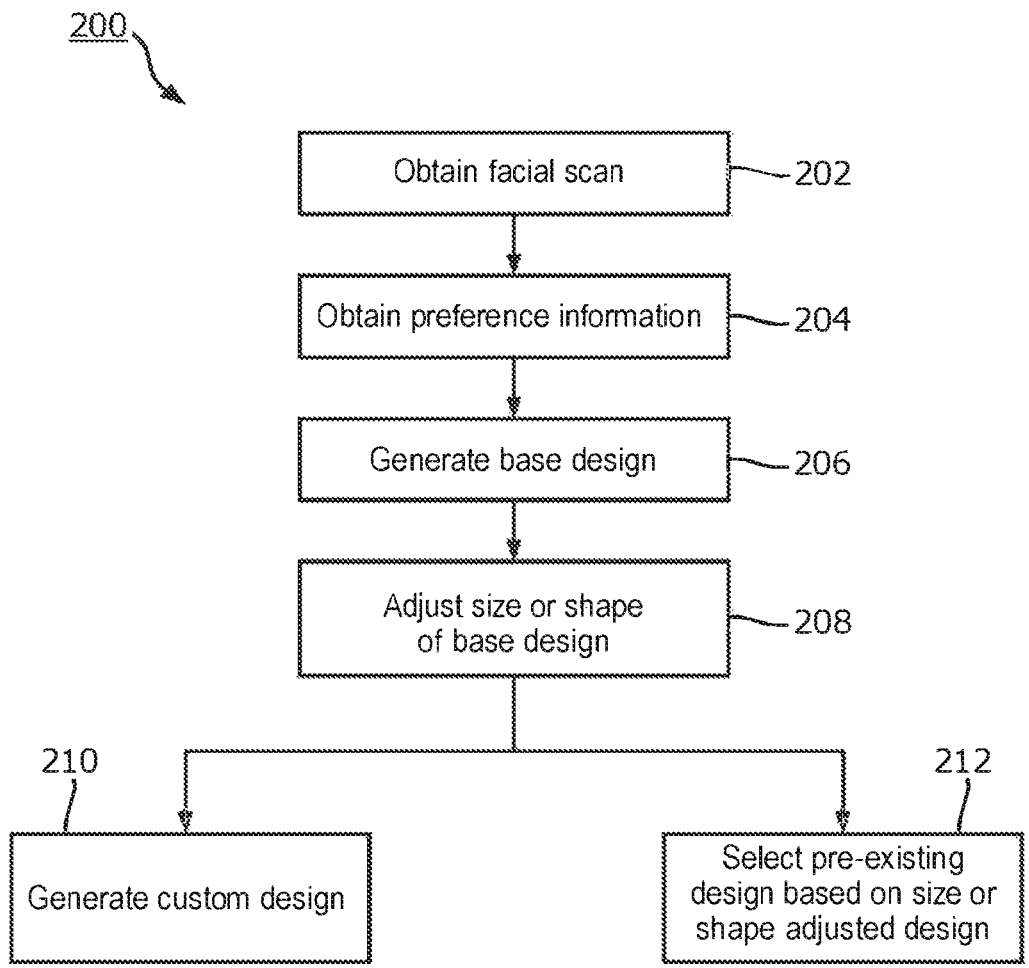
FIG. 3 is a flowchart of a method of selecting or generating a patient interface device component design according to an exemplary embodiment of the disclosed concept.

FIG. 3 is a flowchart of a method 200 of generating or selecting a design for a component of a patient interface device according to an exemplary embodiment of the disclosed concept. The method of FIG. 3 may be implemented, for example, by system 100 of FIG. 2. Method 200 begins at 202 where a scan of a patient's face is obtained. The scan may be obtained by any suitable scanning unit such as, for example, face scanning unit 102. At 204 preference information is obtained from the patient. The preference information may be collected by, for example, patient preference collection unit 104. Any suitable type of preference information, including any of the types of preference information previously described herein, may be obtained.

At 206 a base design for a component of the patient interface device is generated. The base design is generated based on the scan of the patient's face. For example, the base design is generated based on an analysis of the scan of the patient's face. The base design may be custom generated or selected from a set of preexisting options. At 208, a size or shape of the base design is adjusted based on the obtained preference information. The size or shape of the base design may be adjusted based on the preference information, for example, in any of the manners described with respect to FIG. 2, or in any other suitable manner.

From 208, method proceeds to either 210 or 212. At 210, a custom design is generated. The custom design may be generated by adjusting the size or shape of the base design and generating a component design geometry based on adjusted base design. At 212, a preexisting component design is selected based on the size adjusted base design. As described above, the base design may be selected from preexisting designs. Based on the size or shape adjustment to the base design, a new preexisting design may be selected. Based on the selected design at 212, the preexisting design may be ordered for the patient.

Figure 4:
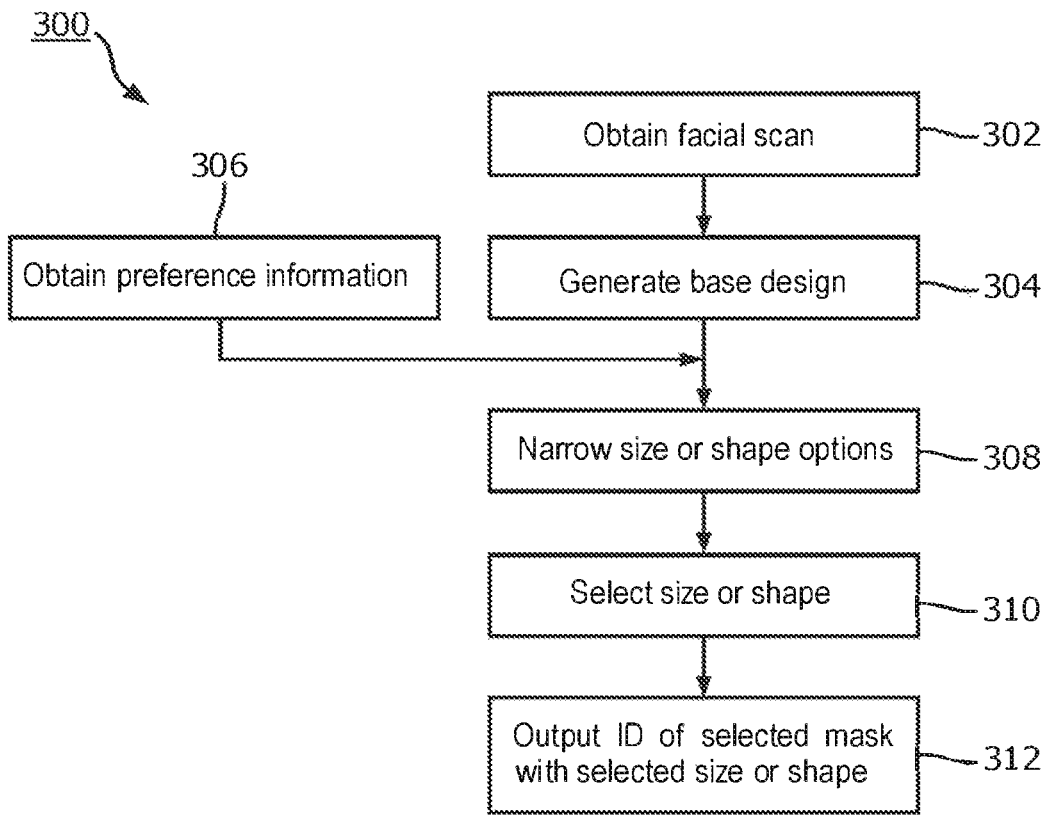
FIG. 4 is a flowchart of a method of selecting a semi-custom patient interface device component design according to an exemplary embodiment of the disclosed concept.

FIG. 4 is a flowchart of a method 300 of selecting a component design for a patient interface device according to an exemplary embodiment of the disclosed concept. The method of FIG. 4 may be implemented, for example, by system 100 of FIG. 2. Method 300 begins at 302 where a scan of a patient's face is obtained. The scan may be obtained by any suitable scanning unit such as, for example, face scanning unit 102. At 304 a base design for a component of the patient interface device is generated. The base design is generated based on the scan of the patient's face. For example, the base design is generated based on an analysis of the scan of the patient's face. The base design may be selected from a set of preexisting options. At 306 preference information is obtained from the patient. The preference information may be collected by, for example, patient preference collection unit 104. Any suitable type of preference information, including any of the types of preference information previously described herein, may be obtained.

At 308 size or shape options for the base design are narrowed. For example, when the base design is selected from a preexisting set of component designs each having a set of size or shape options, the size or shape options for the selected preexisting design may be limited at 308 to a limited set of size options. At 310 a final size or shape option is selected based on the preference information. It will be appreciated that 308 and 310 may be combined into a single step as well without departing from the scope of the disclosed concept. At 312 identification information of the selected design is output. The identification information may be used to order the selected component design for the patient.

Figure 5:
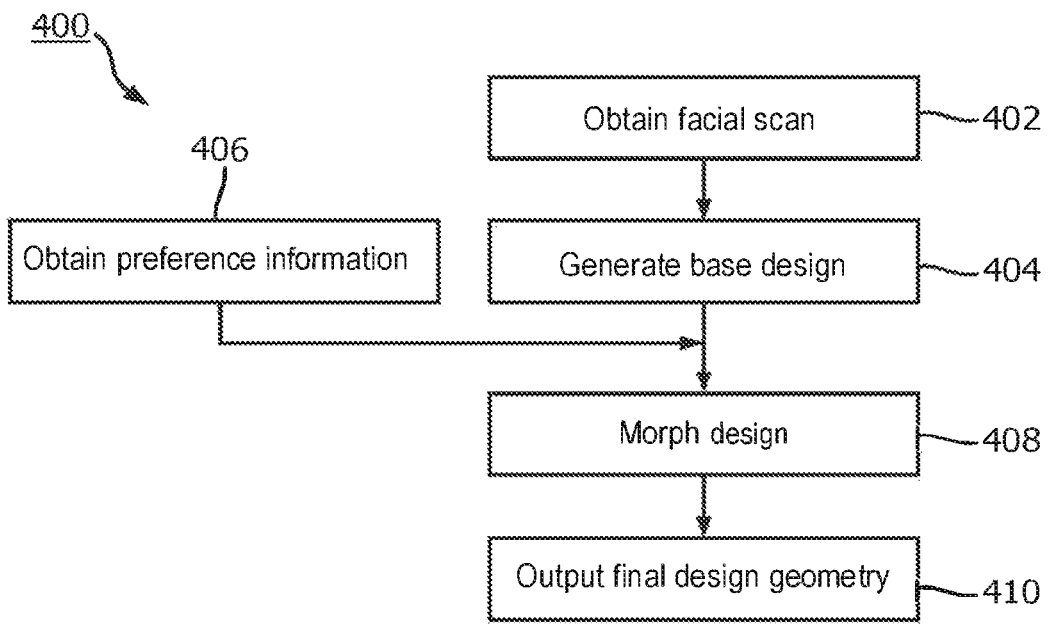
FIG. 5 is a flowchart of a method of generating a custom patient interface device component design according to an exemplary embodiment of the disclosed concept.

FIG. 5 is a flowchart of a method of creating a design for a component of a patient interface device according to an exemplary embodiment of the disclosed concept. The method of FIG. 5 may be implemented, for example, by system 100 of FIG. 2. Method 400 begins at 402 where a scan of a patient's face is obtained. The scan may be obtained by any suitable scanning unit such as, for example, face scanning unit 102. At 404 a base design for a component of the patient interface device is generated. The base design is generated based on the scan of the patient's face. For example, the base design is generated based on an analysis of the scan of the patient's face. The base design may be custom generated. At 406 preference information is obtained from the patient. The preference information may be collected by, for example, patient preference collection unit 104. Any suitable type of preference information, including any of the types of preference information previously described herein, may be obtained.

At 408 the size or shape of the base design is adjusted. For example, the size or shape of the base design may be morphed to change aspects of its size or shape such as its length and/or width, or any other dimension. It will be appreciated that any aspect of the size or shape of the base design of the component may be morphed without departing from the scope of the disclosed concept. At 410 the geometry of the base design is output. The geometry may be output in any suitable manner such as, without limitation, in an electronic format. The geometry may be used to fabricate the component from the custom design.

According to exemplary embodiments described herein, component designs for patient interface devices that are size or shape adjusted based on preference information about the patient may be generated or selected. The designs may be employed in any suitable type of patient interface device and/or pressure support therapy system such as patient interface device 8 and system 2 of FIG. 1, or any other similar system.

While some exemplary embodiments of the disclosed concept have been described with respect to generating or selecting a component design, it will be appreciated that the disclosed concept may be employed to select an entire patient interface as well. For example, component designs may be associated or sold as part of an entire patient interface device. As such, when a component design is selected or generated, the associated patient interface device may also be selected.

In accordance with embodiments of the disclosed concept, the geometry of the patient's face is taken into account as well as preference information obtained from the patient when generating or selecting a component design. When only the geometry of the patient's face is taken into account, the component design may fit well, but the patient may feel discomfort due to the component design not accounting for their preferences. Embodiments of the disclosed concept take into account preference information and adjust the size of the component design based on preference information which results in a component design that is more likely to meet a patient's preference and feel more comfortable to the patient.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of selecting or generating a design for a component of a patient interface device, the method comprising:
   receiving a scan of at least a portion of a patient's face;
   receiving preference information about the patient; and
   generating a custom design or selecting a preexisting design for the component of the patient interface device based on the scan of at least a portion of the patient's face and the preference information, wherein a size or shape of the generated custom design for the component or the selected preexisting design for the component is based on the preference information,
   wherein generating the custom design or selecting the preexisting design for the component comprises:
      generating a base design for the component of the patient interface device based on the scan of at least a portion of the patient's face;
      adjusting a size or shape of the base design for the component based on the preference information; and
      using the size or shape adjusted base design for the component as the generated custom design for the component or the selected preexisting design for the component.

2. The method of claim 1, wherein the preference information includes mask performance importance, and wherein when the mask performance includes a ranking of comfort above a predetermined threshold level, adjusting the size of the base design for the component includes increasing a dimension of the base design for the component by a predetermined amount.

3. The method of claim 1, wherein the preference information includes a type of fit preference, wherein when the type of fit preference is loose, adjusting the size of the base design for the component includes increasing a dimension of the base design for the component by a predetermined amount, and wherein when the type of fit preference is snug, adjusting the size of the base design for the component includes decreasing a dimension of the base design for the component by a predetermined amount.

4. The method of claim 1, wherein the preference information includes a claustrophobia rating, wherein when the claustrophobia rating is above a predetermined threshold level, adjusting the size of the base design for the component includes decreasing a visual size of the base design for the component by a predetermined amount.

5. The method of claim 1, wherein the preference information includes a claustrophobia rating, wherein when the claustrophobia rating is above a predetermined threshold level, adjusting the size of the base design for the component includes increasing a dimension of the base design for the component by a predetermined amount.

6. The method of claim 1, wherein the preference information includes a nose breathing restriction rating, wherein when the nose breathing restriction rating is above a first threshold level, adjusting the size of the base design of the component includes increasing dimension of the base design for the component by a first predetermined amount, wherein when the nose breathing restriction rating is above a second threshold level, adjusting the size of the base design for the component includes increasing a dimension the base design from the component by a second predetermined amount.

7. The method of claim 1, wherein the component of a patient interface device is a cushion.

8. The method of claim 1, wherein adjusting the size or shape of the base design for the component based on the preference information includes morphing the base design for the component to adjust its size or shape.

9. The method of claim 1, wherein selecting a preexisting design for the component includes selecting from a set of preexisting size options of the base design for the component the size option most closely matching the size adjusted base design for the component.

10. A system comprising:
a face scanning unit structured to obtain a scan of at least a portion of a patient's face;
a patient preference collection unit structured to obtain preference information about the patient;
a patient interface selection unit structured to generate a custom design or select a preexisting design for a component of a patient interface device for the patient based on the scan of at least a portion of the patient's face and the preference information, wherein a size or shape of the generated custom design for the component or the selected preexisting design for the component is based on the preference information; and
an output unit structured to output the custom cushion information or the cushion selection information,
wherein the patient interface selection unit is structured to generate a base design for the component of the patient interface device based on the scan of at least a portion of the patient's face, adjust a size or shape of the base design for the component based on the preference information, and to use the size or shape adjusted base design for the component as the generated custom design for the component or the selected preexisting design for the component.

11. The system of claim 10, wherein the component of a patient interface device is a cushion.

12. A non-transitory computer readable medium storing one or more programs, including instructions, which when executed by a computer, causes the computer to perform a method of selecting or generating a design for a component of a patient interface device, the method comprising:
receiving a scan of at least a portion of a patient's face;
receiving preference information about the patient; and
generating a custom design or selecting a preexisting design for the component of the patient interface device based on the scan of at least a portion of the patient's face and the preference information, wherein a size or shape of the generated custom design for the component or the selected preexisting design for the component is based on the preference information,
wherein generating the custom design or selecting the preexisting design for the component comprises:
generating a base design for the component of the patient interface device based on the scan of at least a portion of the patient's face;
adjusting a size or shape of the base design for the component based on the preference information; and
using the size or shape adjusted base design for the component as the generated custom design for the component or the selected preexisting design for the component.

* * * * *